(12) United States Patent
Poland et al.

(10) Patent No.: US 11,719,488 B2
(45) Date of Patent: Aug. 8, 2023

(54) LYOPHILIZATION PROCESS AND A TEVERELIX-TFA LYOPHILIZATE OBTAINED THEREBY

(71) Applicant: Antev Limited, London (GB)

(72) Inventors: Guy Poland, Bristol (GB); Francois Boutignon, Clermont-Ferrand (FR)

(73) Assignee: Antev Limited, London (GB)

( * ) Notice: Subject to any disclaimer, the term of this patent is extended or adjusted under 35 U.S.C. 154(b) by 0 days.

(21) Appl. No.: 17/255,372

(22) PCT Filed: Jul. 2, 2019

(86) PCT No.: PCT/EP2019/067733
§ 371 (c)(1),
(2) Date: Dec. 22, 2020

(87) PCT Pub. No.: WO2020/007860
PCT Pub. Date: Jan. 9, 2020

(65) Prior Publication Data
US 2021/0239397 A1    Aug. 5, 2021

(30) Foreign Application Priority Data

Jul. 5, 2018 (EP) ..................................... 18181960

(51) Int. Cl.
| | | |
|---|---|---|
| A61K 39/395 | (2006.01) | |
| F26B 5/06 | (2006.01) | |
| A61K 9/19 | (2006.01) | |
| A61K 38/09 | (2006.01) | |
| A61K 47/12 | (2006.01) | |

(52) U.S. Cl.
CPC .................. *F26B 5/06* (2013.01); *A61K 9/19* (2013.01); *A61K 38/09* (2013.01); *A61K 47/12* (2013.01)

(58) Field of Classification Search
None
See application file for complete search history.

(56) References Cited

U.S. PATENT DOCUMENTS

2002/0198146 A1* 12/2002 Damm .................... A61P 15/00
514/10.4
2003/0044463 A1    3/2003 Deghenghi et al.

FOREIGN PATENT DOCUMENTS

| WO | WO2003/022243 A2 | 3/2003 |
| WO | WO2008/071984 A1 | 6/2008 |

OTHER PUBLICATIONS

International Search Report and Written Opinion Appl. No. PCT/EP2019/067733, dated Oct. 9, 2019.
International Preliminary Report on Patentability (IPRP), Appl. No. PCT/EP2019/067733, dated Jun. 19, 2020.

* cited by examiner

*Primary Examiner* — Yunsoo Kim
(74) *Attorney, Agent, or Firm* — Fox Rothschild LLP (57) ABSTRACT

The present invention relates to a lyophilization process for preparing a teverelix-TFA lyophilizate, said process comprises the following steps: a) providing a lyophilization suspension by mixing teverelix and trifluoroacetate at a molar ratio sufficient for providing a microcrystalline teverelix-TFA suspension without formation of a gel, and b) lyophilizating the lyophilization suspension, thereby providing a teverelix-TFA lyophilizate.
The process provides the possibility of obtaining a "pure" teverelix-TFA lyophilizate i.e. without any undesirable residues in the composition.

13 Claims, 6 Drawing Sheets

LYOPHILIZATION PROCESS AND A TEVERELIX-TFA LYOPHILIZATE OBTAINED THEREBY

This application is a 371 filing of International Patent Application PCT/EP2019/067733 filed Jul. 2, 2019, which claims priority to European patent application no. 18181960.8 filed Jul. 5, 2018.

TECHNICAL FIELD

The invention relates to a lyophilization process, to a teverelix-TFA lyophilizate obtained by said process, and to a method of reconstituting said teverelix-TFA lyophilizate.

BACKGROUND

Teverelix is a synthetic gonadotropin-releasing hormone antagonists (GnRH antagonists) that compete with the endogenous neurohormone GnRH (otherwise known as luteinizing hormone releasing hormone, LHRH) for binding to its receptors in the anterior pituitary gland. By decreasing or blocking GnRH action, the GnRH antagonist suppress release from the anterior pituitary gland of follicle stimulating hormone (FSH) and luteinizing hormone (LH).

Both FSH and LH are involved in normal reproductive function. In females, FSH stimulates the growth of immature Graafian follicles to maturation, whereas changes in LH levels control ovulation. In males, on the other hand, FSH plays an important role in spermatogenesis and LH stimulates production of testosterone in the testes.

Accordingly, teverelix is suitable for treatment of hormone-dependent conditions such as benign prostatic hypertrophy, hormone-dependent prostate cancer, endometriosis and uterine myomas.

Sustained release formulations usually require very high concentrations of active ingredient dissolved in small volumes water or some other suitable solvent(s). Since teverelix (Ac-D-Nal-D-pClPhe-D-Pal-Ser-Tyr-D-Hci-Leu-Lys(iPr)-Pro-D-Ala-NH$_2$) is a hydrophobic peptide it is not freely soluble in water or in other solvents. Teverelix further has a propensity to form gels in aqueous or other solvents even at low concentrations, which greatly limit its use in sustained release formulations.

WO2003/022243 aims at solving this problem and discloses that the formation of a gel may be prevented by contacting the teverelix peptide with a counter-ion, e.g. trifluoroacetate (TFA). According to WO2003/022243, a ratio of teverelix to the counter-ion trifluoroacetate of at least 1:1.6 is essential in order to ensure the desired microcrystalline suspension is obtained, otherwise a gel will be formed. However, the inventors of the present invention have found that the molar ratios disclosed in WO 2003/022243 will result in both undesirable gel-formation and in suspensions which are not homogenous. This is a problem, not only because such suspensions will be difficult to inject, but also because the bioavailability of the teverelix peptide is compromised since the gel interferes with the desired sustained action of said peptide.

The inventors of the present invention have furthermore discovered that there are batch variations in the molar ratio of teverelix to the counter-ion TFA provided by the manufactures of WO2003/022243, even though the applied manufacturing conditions and processes are identical for said batches. Since the molar ratio is essential for obtaining the desired microcrystalline suspension, variations in said ratio may affect the bioavailability of teverelix in the pharmaceutical formulations. It is therefore essential that medical personal and other users can rely on the molar ratio of teverelix to trifluoroacetate provided by the manufactures.

Another problem with the teverelix compositions of WO2003/022243 is that said compositions are not stable during storage e.g. at refrigeration and room temperatures, and accordingly teverelix has a relatively short shelf life under such conditions.

Lyophilization (freeze drying) is a widely used process for improving the stability of pharmaceuticals, and even thought WO2003/022243 refer to freeze-drying and lyophilization of teverelix, the document only refers to the technique in a general manner such as "the material is freeze-dried over night" and other general statements of similar description, but fails to disclose the specific requirements needed for lyophilization of teverelix-TFA.

Teverelix-TFA has a very low solubility in water and in order to provide a solution that can undergo a lyophilization process the teverelix-TFA has to be dissolved. However, this can only be accomplished in a strong acid, e.g. a concentrated acid. The use of strong acid as a solvent not only requires more attention to the freeze drying process, but lower temperatures are also required to freeze and condense the solvents and said solvents can easily bypass the condenser and end up causing damage to e.g. the vacuum pump. Thus, specialized lyophilization equipments are required in order to prevent damage to the equipment, adding to the overall costs of the lyophilization process.

Furthermore, before lyophilization is initiated it is very important to carefully consider all non-volatile compounds of the sample as these will concentrate along with the relevant active ingredient, i.e. teverelix. Non-volatile acids or bases can cause extreme pH, and the presence of salts can result in very high ionic strength when the sample is resolubilised. It is therefore essential that special care is taken when lyophilising a teverelix composition as the resultant lyophilizate may end up comprising residual acid which will have an adverse effect on the intended use. This adds further complexity to the lyophilization process as it is important that all solvent is removed in the lyophilizate, in order to ensure that the reconstituted teverelix-TFA lyophilizate can be administrated safely to a patient, e.g. by subcutaneous and/or intramuscular injection.

Finally, the viscosity of the teverelix-TFA solution causes the sterilization filters to clog also making the sterilization process laboriously and expensive.

Accordingly, there is a demand to develop a new process of manufacturing a stable and sterile teverelix-TFA lyophilizate having a long shelf life.

SUMMARY OF THE INVENTION

It is therefore a first aspect of the present invention to provide a simple and efficient novel lyophilization process for providing a teverelix-TFA lyophilizate, and wherein the use of strong organic solvents for dissolving the teverelix-TFA is eliminated, it is a second aspect according to the present invention to provide a lyophilization process which does not require a filter sterilization step for providing a sterile teverelix-TFA lyophilizate, it is a third aspect according to the present invention to provide a teverelix-TFA lyophilizate having a higher teverelix-TFA concentration than hitherto known, is a fourth aspect according to the present invention to provide a teverelix-TFA lyophilizate that can be easily resuspended in an aqueous resuspending liquid thereby providing a homogen aqueous teverelix-TFA formulation, it is a fifth aspect according to the present invention to provide a method of adjusting the molar ratio of peptide to counter-ion in the aqueous teverelix-TFA formulation.

These and further aspects are achieved according to the prevent invention by providing a lyophilization process for preparing a teverelix-TFA lyophilizate, said process comprises the following steps:

a) providing a lyophilization suspension by mixing teverelix and trifluoroacetate at a molar ratio sufficient for providing an microcrystalline teverelix-TFA suspension without formation of a gel, and b) lyophilizating the lyophilization suspension, thereby providing a teverelix-TFA lyophilizate.

DETAILED DESCRIPTION OF THE INVENTION

A number of advantages are obtained by using the lyophilisation process according to the present invention. First of all, since higher concentrations of teverelix-TFA (about 100 mg/ml), can be obtained in a microcrystalline teverelix-TFA suspension, compared to the concentration of teverelix-TFA dissolved in a solvent (about 10 mg/ml), a significantly smaller lyophilization volume is required in order to obtain the same quantity of teverelix-TFA. This ensures that the lyophilization step may be conducted faster and more cost-efficient than the conventional lyophilization processes.

Secondly, since it is the microcrystalline teverelix-TFA suspension that is lyophilisated, the need for using strong acids for dissolving the teverelix-TFA is eliminated. Thus, the lyophilization process according to the present invention provides the possibility of obtaining a "pure" teverelix-TFA lyophilizate i.e. without any undesirable residues in the composition, in a fast and simple manner.

In order to obtain a microcrystalline teverelix-TFA suspension, without formation of a gel, the inventors of the present invention have found that a molar ratio of teverelix to the counter-ion trifluoroacetate has to at least 1:2.1, since a molar ratio below 1:2.1 will result in formation of a gel. When the molar ratio is above 1:2.2 the microcrystalline teverelix-TFA suspension is also homogeneous.

Within the content of the present invention the term "molar ratio of teverelix to trifluoroacetate" refers to the molar relationship between teverelix and trifluoroacetate, where the first number of the molar ratio is the mol content of teverelix in the composition and the second number refers to the mol content of TFA in the composition. For instance, a molar ratio of 1:2.2 means that for each mol teverelix in the composition, said composition comprises 2.2 mol TFA, and a molar ratio of at least 1:2.2 means that for each mole teverelix in the composition, the composition comprises at least 2.2. mol trifluoroacetate (TFA).

The obtained teverelix-TFA lyophilizate may be stored and reconstituted with water or another suitable aqueous solution in order to prepare an aqueous teverelix-TFA formulation that e.g. may be used as an injectable pharmaceutical formulation.

However, in order to obtain a more stable teverelix-TFA lyophilizate, or be able to provide a specific said molar ratio in dependence of the intended use, it is desirable to lower the molar ratio, i.e. reduce the content of TFA in said composition, and step a) therefore comprises the following additional steps:

a') centrifuging or filtering the microcrystalline teverelix-TFA suspension from step a), thereby providing a teverelix-TFA pellet or a teverelix-TFA filter cake, and a") suspending said teverelix-TFA pellet or said teverelix-TFA filter cake in an aqueous suspension solution.

Whereas the lyophilization suspension can be directly lyophilizated without the centrifuging step or the filtering step, it is preferred that it is the teverelix-TFA pellet or teverelix-TFA filter cake obtained after the microcrystalline teverelix-TFA suspension has been centrifuged or filtered which is suspended and then subjected to a lyophilization step.

The inventors of the present invention have found that if the microcrystalline teverelix-TFA suspension has a molar ratio above 1:2.1 (which is the molar ratio in which no gel is obtained), the molar ratio in the pellet or filter cake after centrifugation will be reduced to a molar ratio between 1:1.70 and 1:1.85. For instance, the inventors found that when the teverelix and trifluoroacetate was mixed at a molar ratio of 1:2.2 and with a peptide concentration of 75 mg/ml, the pellet after centrifugation had a molar ratio of about 1:1.77.

Thus, the centrifugation/filtration and suspension steps of the lyophilization process according to the invention provides the advantages that the resultant teverelix-TFA lyophilizate will have a predefined molar ratio which is lower than the molar ratio of the microcrystalline teverelix-TFA suspension, thereby ensuring that the molar ratio can be adjusted to any desired molar ratio (above the initial molar ratio) when the lyophilizate is reconstituted. Furthermore, since the lyophilizate has a reduced content of the counter-ion trifluoroacetate, the pH value in the lyophilizate is maintained at a value which ensures that a possible deamidation of teverelix is reduced, whereby the stability of teverelix during storage is increased.

In order to reduce the volume on which the lyophilization is to take place, and at the same time ensure a high concentration of teverelix in the resultant lyophilizate, the microcrystalline teverelix-TFA suspension is in one embodiment centrifuged under conditions sufficient for ensuring that a pellet is formed. The pellet is then suspended in a relatively small amount of aqueous suspension solution, and the lyophilization suspension is then the suspended pellet However, the inventors of the present invention have found, that if a teverelix-TFA filter cake is obtained by filtering the microcrystalline teverelix-TFA suspension (instead of centrifuging said suspension and providing a teverelix-TFA pellet), the aqueous teverelix and the excess of TFA will pass through the filter, and only the solid teverelix (microcrystals), at a low molar ratio i.e. a molar ratio between 1:1.70 and 1:1.85, will be collected on the filter. Thus, use of a filtering step for providing a teverelix-TFA cake provides a lyophilized product consisting essentially of microcrystals from the microcrystalline teverelix-TFA suspension, and therefore provides an improved final teverelix-TFA lyophilizate.

Any kind of filtering technique may in principal be used for obtaining the teverelix-TFA filter cake, however it is preferred to use a pressure or vacuum filter technique using a suitable filter, e.g. a 0.45 to 0.8 μm membrane filter, as such a filter is capable of both allowing the viscose teverelix-TFA suspension to pass and effectively holding the microcrystals back.

The inventors have further found that by first providing a pellet or filter cake and then suspending said pellet or cake in an aqueous suspension solution, the need for using strong acids for dissolving the teverelix-TFA is surprisingly eliminated. The aqueous suspension solution for suspending the pellet or filter cake may in a preferred embodiment be either water or a mannitol solution, e.g. a 5% mannitol solution, thus if small residues of the solvent remains in the lyophilisate, this will not influence the lyophilisates ability to be used in a pharmaceutical formulation.

Irrespectively of the microcrystalline teverelix-TFA suspension is subjected to a centrifugation or filtering step, it is preferably that the microcrystalline teverelix-TFA suspension in step a) is made in either water, e.g. physiological water, or in a trifluroacetic acid solution. However, if the molar ratio of teverelix to trifluoroacetate is at least 1:2.2 it is preferred that the teverelix-TFA suspension is made in water, and if said molar ratio is below 1:2.2 it is preferred that the suspension is made in a trifluroacetic acid solution in order to add trifluroacetic acid to the suspension in order to obtain a molar ratio of at least 1:2.2.

The molar mass of trifluoroacetate and teverelix has been calculated to: $M_{TFA}$=114 g/mol and $M_{Tev}$=1459 g/mol, and the molar ratio and/or content of trifluoroacetate or teverelix in the suspension can accordingly be calculating using the following formula:

$$\text{Molar ratio} = \frac{\text{trifluoroacetate content in suspension}/M_{TFA}}{\text{teverelix content in suspension}/M_{Tev}}$$

In order to ensure a high teverelix concentration in the teverelix-TFA lyophilizate, it is preferred that the concentration of teverelix-TFA in the microcrystalline teverelix-TFA suspension in step a) is at least 100 mg/ml. If the suspension thereafter is centrifugated, a high teverelix concentration further has the advantage that less peptid will be discarded with the supernatant.

Lyophilization is a process well known in the art, and said process will not be discussed in details in the present application. However, in short, the sample, i.e. the lyophilization suspension (which may either be the microcrystalline teverelix-TFA suspension or the suspended pellet or the filter cake), is transferred into one or more glass container(s) and is frozen as quickly as possible, e.g. by immersing the outside of the container into liquid nitrogen or by using electrically powered freezers. Moreover, the container(s) may optionally be rotated in order to spread and freeze the sample on a large surface area. The glass container(s) with the sample is then preferably placed into an extremely low-pressure space (vacuum) that contains a cooling coil as well. The cooling coil acts as a condenser. The temperature of the coil is usually lower than −50° C. Volatile compounds of the frozen sample will evaporate (sublimate) in the vacuum. The process of evaporation (in this case, sublimation) absorbs heat. This effect keeps the sample frozen. Evaporated molecules are captured from the gas phase by the cooling coil, forming a frozen layer on it. At the end of the process, the teverelix-TFA remains in the container in a solid form. Since this process does not cause degradation of teverelix, the lyophilization process according to the invention may not only be used to concentrate the teverelix, but may also be used to preserve said peptide for long-term storage.

A person skilled in the art will in view of the present invention understand that instead of subjecting the lyophilization suspension from step a) to a lyophilization process, said suspension may in a modified process according to the invention be subjected to a spray-drying process or similar drying process, in order to obtain a powder and/or a powder like product.

Since lyophilization is carried out on a lyophilization suspension made in water or mannitol, said suspension does not comprise any harmful non-volatile compounds, e.g. non-volatile acids that may can cause extreme pH-values, and salts that may result in very high ionic strength. Accordingly, the resultant lyophilizate will not contain any undesirable compounds, and a resuspended aqueous teverelix-TFA suspension can safely be administrated to a patient in need of such treatment.

In most conventional lyophilizations the solution to be freeze-dried is initially filtered aseptically to remove any extraneous solids and microorganism. However, since the viscosity of the teverelix-TFA solution causes the sterilization filters to clog such a sterilization step in both laboriously and expensive. The inventors of the present invention have found that the teverelix-TFA lyophilizate obtained by the process according to the present invention may be subjected to gamma sterilization, thereby eliminating the requirement for filter sterilization. Furthermore, the requirement for working under aseptic conditions e.g. in a clean room, is also eliminated.

Normally a lyophilizate is stored in a substantially dry state in order to maintain the stability of the composition. The inventors of the present invention have however found that if a small amount of water is present in the teverelix-TFA lyophilizate according to the invention, i.e. in an amount between 0.3% to 5% by weight, preferably around 1 to 2% by weight, based on the total weight of the teverelix-TFA lyophilizate, an improved teverelix-TFA lyophilizate is provided which is easier to handle, reconstitute, and accordingly use.

Without being bound by theory, the water content may provide high electrostatic forces between particles of teverelix, which is of importance when the teverelix-TFA lyophilizate is handled e.g. if the lyophilizate are to be filled to a vial or a syringe chamber.

In a preferred embodiment water is present in the teverelix-TFA lyophilizate in an amount between 1% by weight and 2% by weight, preferably 1.5% by weight, based on the total weight of the teverelix-TFA lyophilizate, as this will provide a teverelix-TFA lyophilizate that retains its chemical integrity and provides a stable composition.

The stability provided by the invention enables a longer shelf-life at room temperature so that the teverelix-TFA lyophilizate may be stored e.g. after sterilization. The reconstitutable teverelix-TFA lyophilizate can be packaged and stored (e.g. in a syringe or vial) for later use.

Due to electrostatic forces between dry particles of teverelix it may be difficult to transfer the teverelix-TFA lyophilizate to a vial, container or a syringe chamber, as the particles will stick to surfaces of equipment etc. It is accordingly preferred that before the suspended pellet or suspended filter cake is subjected to lyophilization, i.e. dried, said suspended pellet/filter case i.e. when it is in an aqueous state is either placed in, or otherwise transferred to, a vial or container in which the suspended pellet or suspended filter cake may be subjected to lyophilization. It is further preferred that said vial or container also can be used for storing the resultant teverelix-TFA lyophilizate.

In a preferred embodiment the vial or container will contain a unit dosage of the teverelix-TFA lyophilizate after lyophilization. Within the context of the present invention the term "unit dosage" is the amount of teverelix administered to a patient in a single dosage.

The present invention also relates to a method of reconstituting the teverelix-TFA lyophilizate, and wherein said method comprises adding an aqueous reconstitution solution to the teverelix-TFA lyophilizate, and adjusting the molar ratio of the molar ratio of teverelix to trifluoroacetate by adding trifluoroacetate. Said method will effectively and simply achieve an exact and desired molar ratio in order to obtain the fluid, milky microcrystalline aqueous suspension of teverelix-TFA, without formation of a gel. It is preferred that the molar ratio of teverelix to TFA after reconstitution is adjusted to at least 1:2.1, preferably at least 1:2.2 and even more preferred at least 1:2.4 by adding a sufficient amount of trifluoroacetate as this will provide an aqueous pharmaceutical formulation that may be used directly, i.e. the formulation is ready-to-use.

The trifluoroacetate content may be added/adjusted after the lyophilizate is reconstituted, but in a preferred embodiment the trifluoroacetate is part of the aqueous reconstitution solution, as this will ensure a fast and effective way of reconstituting the teverelix-TFA lyophilizate according to the invention. If desired, the aqueous reconstitution solution may contain an isotonic agent, such as mannitol and/or a pharmaceutically acceptable excipient.

The correct amount of trifluoroacetate to be added may easily be calculated for a person skilled in the art. For instance, if the teverelix-TFA lyophilizate has a molar ratio of 1:1.77, and if a molar ratio of 1:2.2 is desired in the final aqueous teverelix-TFA formulation, then 0.43 mol TFA per mol teverelix present in the composition has to be added during the reconstitution process.

The inventors of the present invention have furthermore found that when the molar ratio of teverelix to trifluoroacetate is at least 1:2.1 in the final aqueous pharmaceutical formulation, the formulation will comprise both soluble and insoluble teverelix, thereby providing a unique bioavailability of teverelix.

Without being bound by theory, the soluble teverelix is in the form of an aqueous solution and in some situations, a gel. The presence of a gel will inhibit any freely aqueous teverelix and therefore prevent, or at least reduce, immediate release. The insoluble teverelix is in the form of microcrystals. Said microcrystals will prevent gel formation, therefore "unlocking" the aqueous teverelix. Over time the TFA in the composition according to the invention will be absorbed by the body, lowering the ratio, so the microcrystals subsequently turn in to gel, which forms the slow release depot. Thus, the non-gel-soluble teverelix is immediately available, providing an almost immediate onset of action, and the gel-soluble and insoluble teverelix (microcrystals) will assist in providing a sustained release of teverelix.

Accordingly, using the teverelix-TFA lyophilizate according to the invention, it is possible to adjust the release profile of teverelix simply by adjusting the amount of trifluoroacetate added to the teverelix-TFA lyophilizate and thereby change the ratio of insoluble to soluble teverelix in the injected formulation.

Since teverelix is deamidated when placed in contact with acid, undesirable degradation products (impurities) will appear within the composition/formulation during storage. Said impurities may influence quality, safety and efficacy of the teverelix composition/formulation, thereby potentially causing serious health hazards.

The inventors of the present invention have found that the level of impurities are kept at an acceptable level, when the molar ratio of teverelix to TFA is at or below 1:2.8, i.e. when the molar content of TFA is at or below 2.8 per mol teverelix. Thus, the optimal molar ratio in the teverelix-TFA lyophilizate according to the invention is preferably between 1:2.2 (or 1:2.4) and 1:2.8.

In a preferred embodiment the invention also relates to a kit, comprising a first package filled with a unit dosage of teverelix and a second package filled with a reconstitution solution comprising a sufficient amount of TFA for obtaining the desired molar ratio of at least 1:2.1, preferably at least 1:2.2 and even more preferred about or above 1:2.4, optionally with a molar ratio at or below 1:2.8 Said first package may e.g. be a syringe and the second package be physically connected to said syringe in order to ensure that the correct molar ratio of teverelix to TFA is obtained. As one example of a first and second package which is physically connected to each other can be mentioned a conventional dual chamber syringe for lyophilised products. Such dual chamber syringe is well known in the art.

In one embodiment said kit is arranged for providing a final fluid, milky microcrystalline aqueous teverelix-TFA suspension having a molar ratio of teverelix to counter-ion of at least 1:2.1, preferably at least 1:2.2 and even more preferred about or above 1:2.4, and optionally at or below 1:2.8. Preferably the concentration of teverelix is between 30 mg/ml and about 100 mg/ml, and even more preferred between 45 mg/ml and 90 mg/ml, e.g. about 75 mg/ml. The concentration of teverelix may in some situations be higher than about 100 mg/ml. The volume may be between 0.4 ml and 1.6 ml, e.g. about 1.2 ml. Injection given subcutaneous and/or intramuscularly at this concentration and volume, has proven to only provide a mild injection site reaction.

The lyophilizates and formulations provided in the present invention is inexpensive to manufacture, and due to the ease of use they provide a very simple dosage regime.

EXAMPLES

In order to establish the influence of the molar ratio of teverelix to the counter-ion trifluoroacetate a number of tests were performed.

Example 1: Preparation of Teverelix-TFA Compositions with Different Molar Ratio A custom-manufactured batch of teverelix with low TFA content, Batch A, was obtained. The characteristics of the batch are shown in table 1.

$$\frac{75 \text{ mg teverelix}}{99.3/100 \text{ (\% purity)} \times 85.56/100 \text{ (\% teverelix)}} = 88.28 \text{ mg content}$$

If a composition A containing 75 mg teverelix is desired, then 88.28 mg of batch A has to be used, calculated as follows:

TABLE 1

| | |
|---|---|
| Purity | 99.3 % |
| Teverelix content | 85.56 weight- % |
| TFA content | 10.9 weight- % |
| Acetate content | 0.3 weight- % |
| Water content | 4.3 weight- % |

The molar ratio of teverelix to TFA in composition A can then be calculated.

The TFA content in 88.28 mg of batch A can be calculated to 88.28 mg×10.9/100 (TFA content in %)=9.62 mg Since the molar mass of TFA, $M_{TFA}$, is 114 g/mol, and the molar mass of teverelix, $M_{TEV}$, is 1459 g/mol, the molar concentration in the 75 mg teverelix composition of TFA can be calculated to 0.084 mmol and the molar concentration of teverelix to 0.051 mmol. Thus, the molar ratio of teverelix to TFA in composition A, is 1:1.64.

In order to prepare a number of different aqueous teverelix-TFA compositions with different molar ratios, twenty-one samples containing 44.14 mg+5% (41.93 to 46.35 mg) of composition A were accurately weighed in 2 ml glass tubes having a cap through which an aqueous solution could be added by means of a micropipette.

Seven TFA solutions containing TFA in 5% mannitol were prepared using a TFA composition obtained from Acros Organics, Geel, Belgium. Said TFA composition were 99% pure and had a density of 1.535 g/ml. The respective solutions are shown in Table 2.

TABLE 2

| Solution | A | B | C | D | E | F | G |
|---|---|---|---|---|---|---|---|
| TFA mol/L | 0 | 0.01 | 0.023 | 0.036 | 0.049 | 0.062 | 0.075 |

The respective aqueous teverelix-TFA compositions were prepared by adding 0.5 ml of each of the above solutions though the cap of the twenty-one glass tubes containing 44.14 mg+5% (41.93 to 46.35 mg) of composition A using a micropipette, i.e. three aqueous teverelix-TFA compositions having the same molar ratio were prepared. The mixtures were stirred using a vortex for 1 minute, and the solutions were observed visually for 10 minutes in order to establish if the desired fluid, milky microcrystalline homogeneous aqueous suspension of the teverelix-TFA, were obtained, or if a gel was formed instead. The results are summarized in Table 3 below:

TABLE 3

| Tubes | Molar ratio | Formation of gel | Microcrystalline formation | Formation of milky suspension | homogeneous suspension |
|---|---|---|---|---|---|
| A1, A2, A3 | 1:1.64 | yes | no | no | — |
| B1, B2, B3 | 1:1.85 | yes | no | no | — |
| C1, C2, C3 | 1:2.1 | no | yes | yes | no |
| D1, D2, D3 | 1:2.36 | no | yes | yes | yes |
| E1, E2, E3 | 1:2.61 | no | yes | yes | yes |
| F1, F2, F3 | 1:2.86 | no | yes | yes | yes |
| G1, G2, G3 | 1:3.12 | no | yes | yes | yes |

The microcrystalline content of the aqueous teverelix-TFA compositions in the No. 1 test tubes were further observed under a polarized light microscope supplied by Realux, France. The results for the respective molar ratio are shown in FIG. 1a-FIG. 1g. From these observations it is clear that microcrystalline formation is not observed for the molar ratios of 1:1.85 and below, thus the molar ratio of teverelix to the counter-ion TFA has to be above at least 1:2.1 in order for the desired microcrystalline formation to be initiated.

Furthermore, as is evident from table 3, a homogeneous suspension of teverelix-TFA was not obtained until the molar ration was above 1:2.1. Thus, it is accordingly preferred that the molar ratio in both the microcrystalline teverelix-TFA suspension used for providing the lyophilization suspension; and the reconstituted aqueous teverelix-TFA suspension is above 1:2.1 and preferably even higher such as at least 1:2.2, and even more preferred at least 1:2.4.

Example 2: Content of Soluble Teverelix and Insoluble Teverelix in Relation to the Molar Ratio In order to determine the content of soluble teverelix in relation to insoluble teverelix in the respective test tubes, the No. 2 and No. 3 test tubes for each molar ratio were centrifuged at 10,000 rpm for 10 to 20 minutes, and the concentration of teverelix in the supernatant and pellet were measured using a HPLC analysis.

The chromatographic conditions for the HPLC analysis is shown in table 4.

TABLE 4

| Column | Type (Aptys N°) | Lichrospher 100 RP18 (N°128) |
|---|---|---|
| | Particles size | 5 μm |
| | Diameter | 4 mm |
| | Length | 125 mm |
| Pre-Column | Type | Lichrocart 100 RP18 |
| | Particles size | 5 μm |
| | Diameter | 4 mm |
| | Length | 4 mm |
| Mobile Phase | | Acetonitrile/Water/TFA (35:65:0.1 V/V/V) |
| Injector cleaning | | Acetonitrile/Water (50:50 V/V) |
| Flow | | 1.0 mL/min |
| Pressure | | Approx. 65 bars |
| Oven Temperature | | 30° C. |
| Wavelength | | 210 nm |
| Injection volume | | 10 μL |
| Injector temperature | | 20° C. |
| Retention time of Teverelix | | Approx. 5.6 min |
| Run time | | 10 min |

Two 100% standards were prepared by weighing 59.9 mg teverelix acetate (batch 080113) in a volumetric flask and completing the volume to 100 ml with water:acetonitrile 65:35 v/v. 10 ml of this solution were completed to 50 ml with the same solvent, providing a concentration of 0.1 mg/ml teverelix peptide.

A 1% standard solution was prepared by diluting 2 ml of the 100% standard to 200 ml with the same solvent providing a concentration of 0.001 mg/ml teverelix peptide.

Internal standardization was carried out using the two 100% standards. The 1% standard was used to check the linearity of the response. Recovery with the 100% standard must be in the interval 95%-105%.

The pellet obtained after centrifugation was solubilised in water:acetonitrile 65:35 v/v, and the volume was completed to 100 mL with the same solvent. This solution was diluted by 5 (10 mL in 50 mL) and HPLC was performed.

The supernatant was transferred to a volumetric flask and the volume was completed to 100 mL with the same solvent, i.e. water:acetonitrile 65:35 v/v. This solution was diluted by 5 (10 mL in 50 mL) and HPLC was performed. The results of the HPLC analysis is shown in table 5.

TABLE 5

| Test tube | Molar ratio | Supernatant-Teverelix concentration (mg/ml) | Pellet-Teverelix concentration (mg/ml) |
|---|---|---|---|
| A2 | 1:1.64 | 52.0 | N/A |
| A3 | 1:1.64 | 58.5 | N/A |
| B2 | 1:1.85 | 57.2 | N/A |
| B3 | 1:1.85 | 60.3 | N/A |
| C2 | 1:2.1 | 25.9 | 26.9 |
| C3 | 1:2.1 | 26.1 | 25.5 |
| D2 | 1:2.36 | 9.4 | 39.3 |
| D3 | 1:2.36 | 8.3 | 44.9 |
| E2 | 1:2.61 | 5.4 | 50.8 |
| E3 | 1:2.61 | 7.2 | 51.6 |
| F2 | 1:2.86 | 3.7 | 56.2 |
| G3 | 1:2.86 | 3.6 | 58.4 |
| G2 | 1:3.12 | 1.5 | 53.6 |
| G3 | 1:3.12 | 1.2 | 58.4 |

Figure 1A:
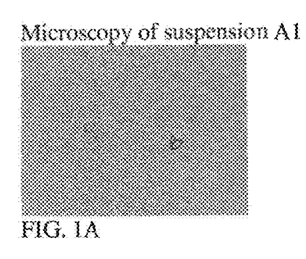
FIGS. 1A-1G show molar ratio results in accordance with one or more embodiments of the present invention.
Figure 1B:
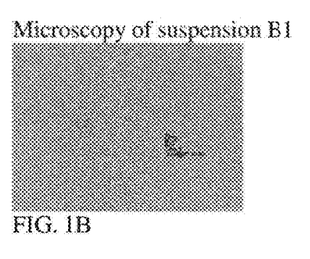
Figure 1C:
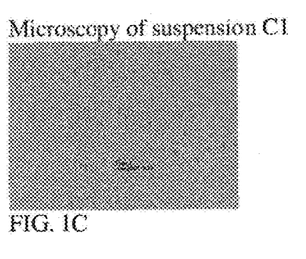
Figure 1D:
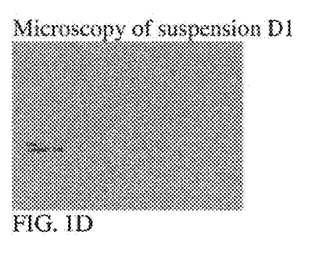
Figure 1E:
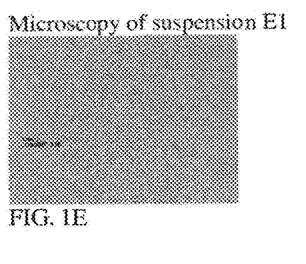
Figure 1F:
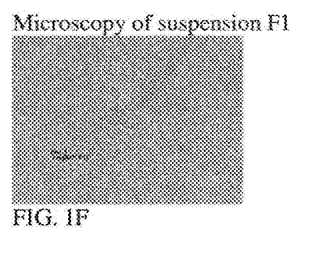
Figure 1G:
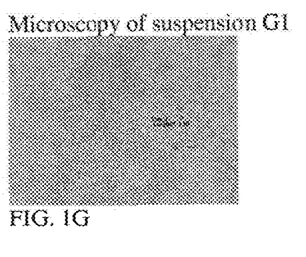
Figure 2:
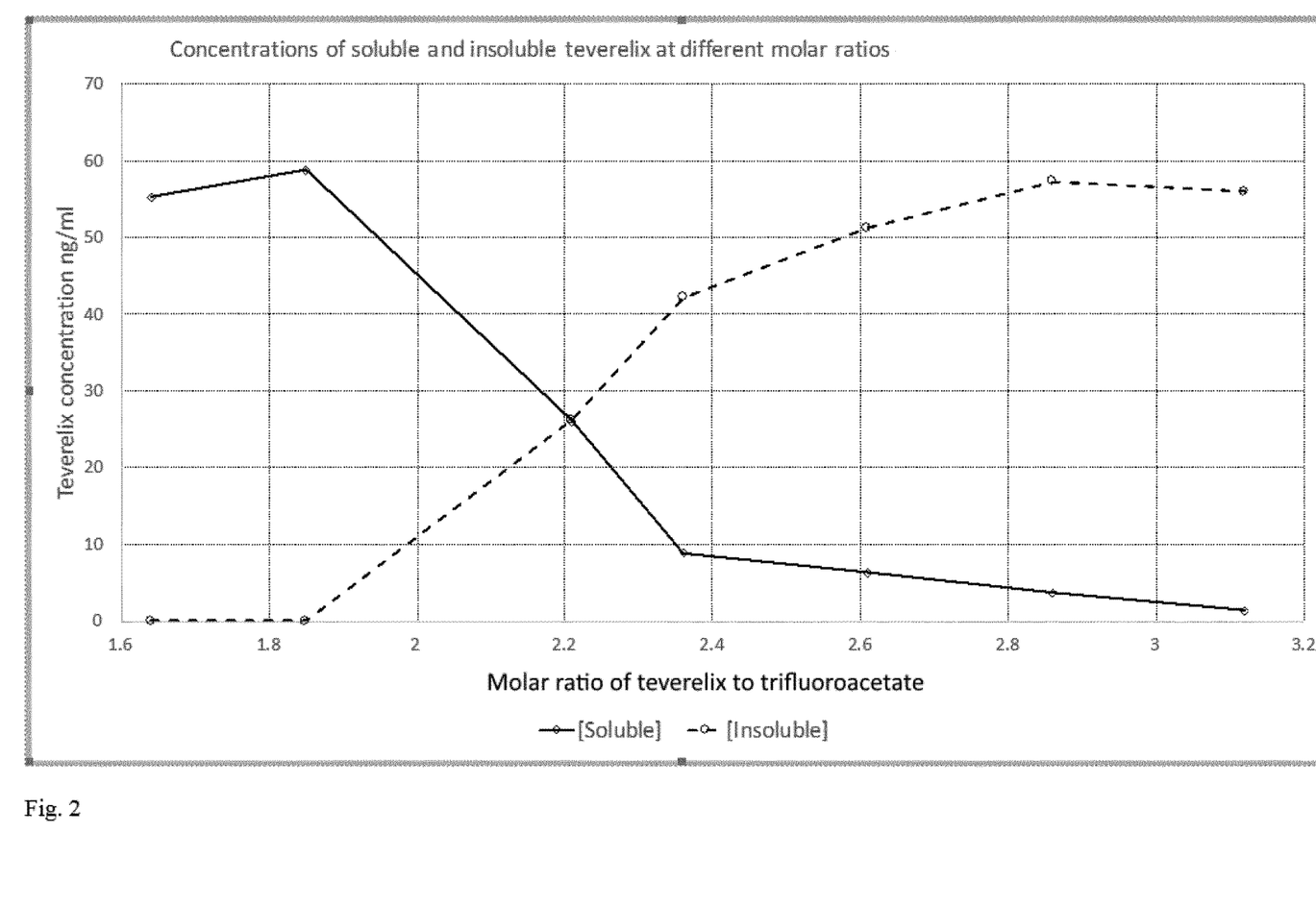
FIGS. 2 and 3 depict the results of Table 6 in accordance with one or more embodiments of the present invention.
Figure 3:
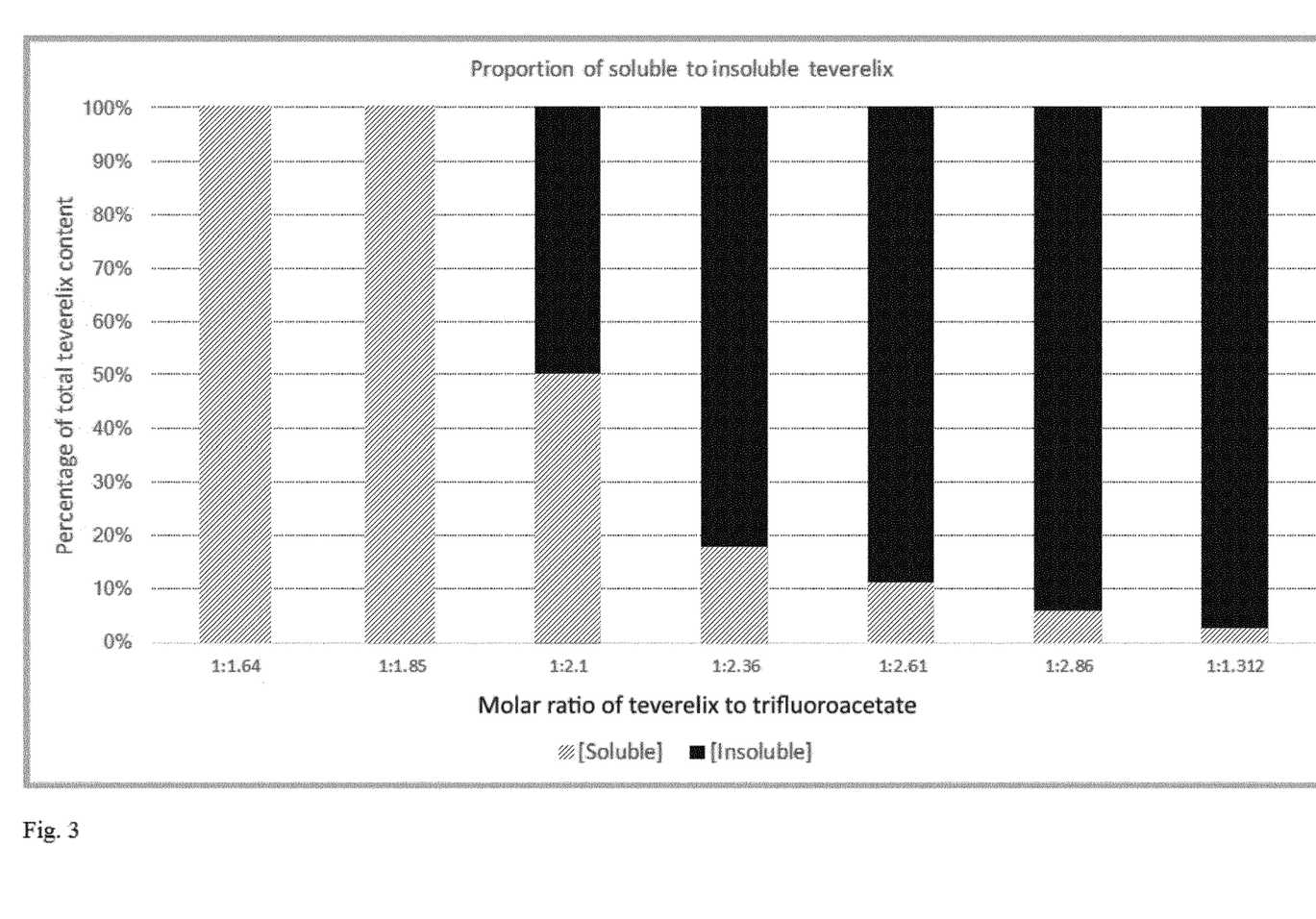

The average concentrations of each molar ratio was calculated, see table 6, and the results are depicted in FIGS. 2 and 3.

TABLE 6

| Test tube | Molar ratio | Supernatant-Average Teverelix concentration (mg/ml) | Pellet-Average Teverelix concentration (mg/ml) | Total (pellet + supernatant) Teverelix concentration (mg/ml) |
|---|---|---|---|---|
| A | 1:1.64 | 55.3 | N/A | 55.3 |
| B | 1:1.85 | 58.8 | N/A | 58.8 |
| C | 1:2.1 | 26.0 | 26.2 | 52.2 |
| D | 1:2.36 | 8.9 | 42.1 | 51.0 |
| E | 1:2.61 | 6.3 | 51.2 | 57.5 |
| F | 1:2.86 | 3.7 | 57.3 | 61.0 |
| G | 1:3.12 | 1.4 | 56.0 | 57.4 |

As is evident from table 5, and 6, and FIGS. 2 and 3, the degree of insoluble teverelix increases when the amount of trifluoroacetate increases in relation to teverelix, thus at a molar ratio of 1:2.1, about 50% of the pharmaceutical formulation consist of insoluble teverelix, whereas the amount of insoluble teverelix is about 82% at a molar ratio of 1:2.36 (~1:2.4) in the pharmaceutical formulation.

Example 3: Plasma Concentration in Relation to the Molar Ratio

In order to evaluate the relevance of the molar ratio on the plasma concentration of teverelix, five glass vials containing different molar ratios were prepared as discussed in example 1, and the test tubes comprising the aqueous teverelix-TFA compositions shown in table 7 were provided:

TABLE 7

| Tube | I | II | III | IV | V |
|---|---|---|---|---|---|
| Molar ratio | 1:1.64 | 1:2.1 | 1:2.36 | 1:2.61 | 1:2.86 |

Five rats were tested with each molar ratio. Each rat was injected with 60 µl of the respective solutions using a 25 mm 21G luer 6% regular bevel needle (obtainable from Terumo, Leuven, Belgium) and 100 µl luer slip syringe (obtainable from Hamilton Company, Reno, USA). Plasma concentrations were measured prior to administration, then at 1 h, 6 h, 24 h, 48 h, 7 days, 10 days, 14 days, 21 days and 28 days following administration.

Figure 4:
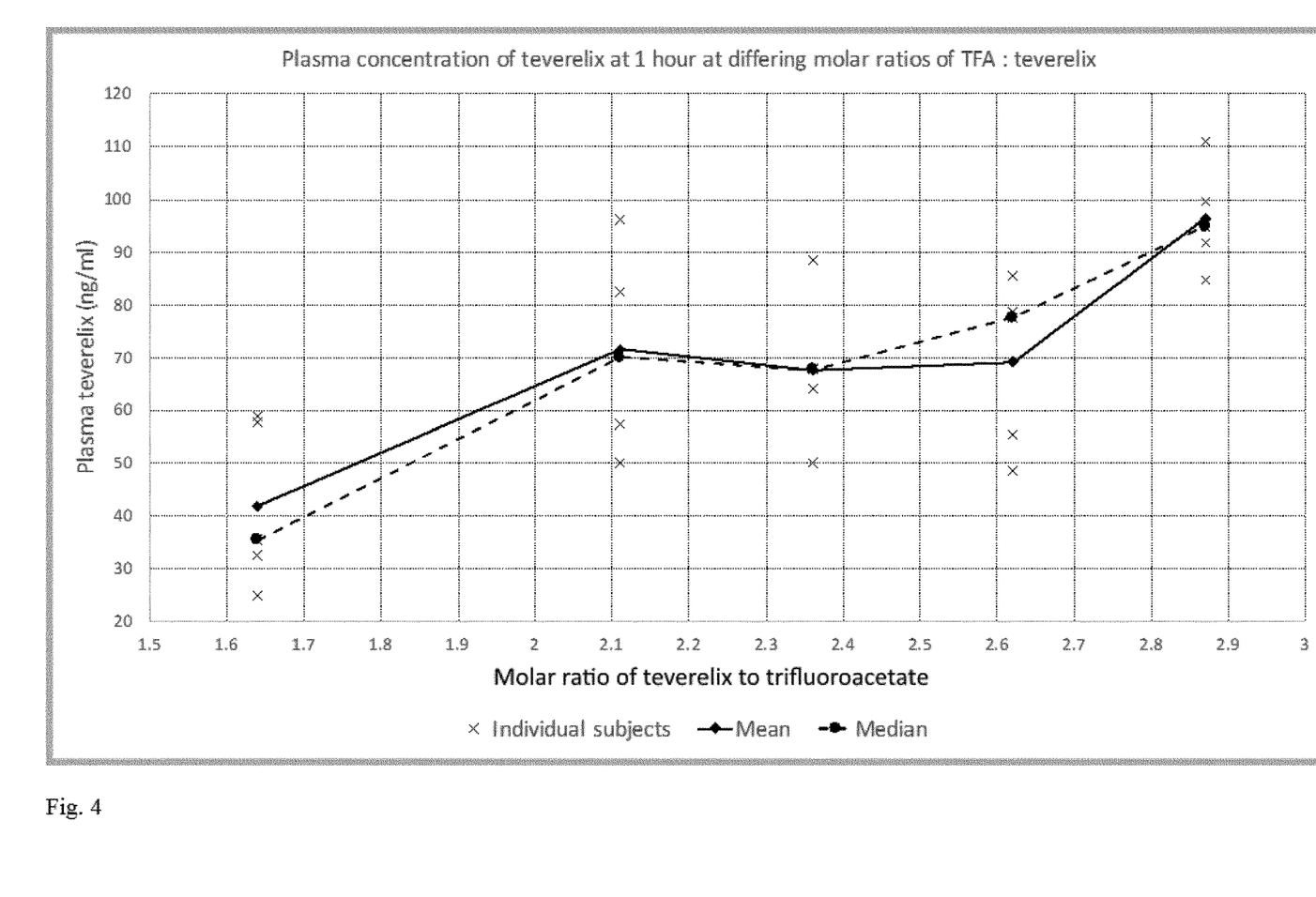
FIG. 4 depicts the results of Table 8 in accordance with one or more embodiments of the present invention.

The peak plasma concentrations, Cmax, of teverelix after injection to each individual rat are shown in table 8, and depicted in FIG. 4.

TABLE 8

| Test tube | Molar ratio | Cmax | Cmax | Cmax | Cmax | Cmax | Cmax mean | Cmax median |
|---|---|---|---|---|---|---|---|---|
| I | 1:1.64 | 57.6 | 58.8 | 35.4 | 32.5 | 25 | 41.86 | 35.4 |
| II | 1:2.1 | 96 | 82.6 | 57.4 | 50.1 | n.a. | 76.525 | 70 |
| III | 1:2.36 | 67.6 | 50 | 67.9 | 64.2 | 88.6 | 67.66 | 67.6 |
| IV | 1:2.61 | 78.8 | 48.6 | 85.5 | 77.5 | 55.3 | 69.14 | 77.5 |
| V | 1:2.86 | 111 | 99.7 | 94.9 | 91.9 | 84.8 | 96.46 | 94.9 |

As is clear from these results the Teverelix Cmax increases until a molar ratio of 1:2.1 after which the plasma concentration is substantially stable.

The plasma concentration over a four week period, was also measured by taking blood samples at regular intervals.

Figure 5:
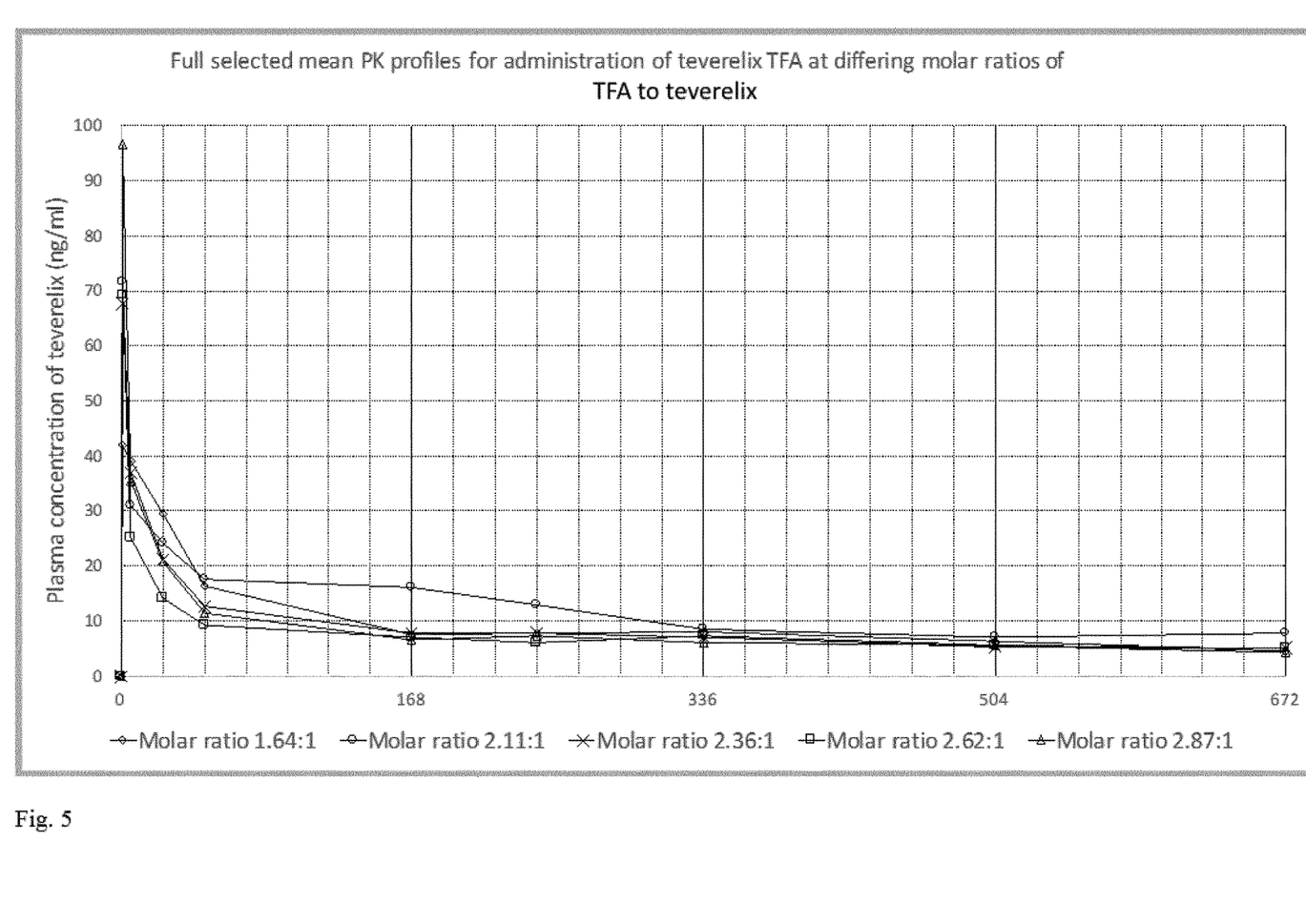
FIG. 5 depicts mean plasma levels in a four week in accordance with one or more embodiments of the present invention.

The mean plasma levels in a four weeks period is shown in FIG. 5, and it is clear that the release profile of teverelix is dependent on the molar ratio. For instance a higher plasma concentration of teverelix is shown with the suspension having a molar ratio of 1:2.1. Thus, it is possible to adjust the release profile of teverelix simply by adjusting the amount of trifluoroacetate added to the teverelix-TFA lyophilizate during reconstitution, thereby changing the molar ratio of teverelix to trifluoroacetate in the pharmaceutical formulation.

Clinically this offers the potential of optimizing the therapy to the requirements of individual groups of patients e.g. relating to different indications, age and/or gender. One patient group may need an immediate onset of action, requiring a high concentration of soluble teverelix, whereas another group may require a sustained release of teverelix, requiring a low concentration of soluble teverelix. In a similar manner, different pharmaceutical formulations having different molar ratios may be administered at different stages of a patients treatment. Furthermore, the possibility of adjusting the molar ratio to specific needs of different patient groups, will increase patient acceptance and compliance of therapy.

Example 4: Stability of Teverelix in Relation to the Molar Ratio

In order to establish the influence of the molar ratio of teverelix to the counter-ion trifluoroacetate on the stability of teverelix, the following test was performed.

Four batches of teverelix TFA solutions were prepared with differing molar ratios of teverelix to TFA (low: 1:1.7; mid-range: 1:2.16; high 1:2.8; and extreme: 1:4.0) at two concentrations: 10 mg/mL (expressed as base teverelix) and 1 mg/mL (expressed as base teverelix).

A reconstitutable Teverelix TFA composition, supplied as a dried powder, was obtained. The characteristics of the batch are shown in table 9:

TABLE 9

| Teverelix content | 79.8% |
|---|---|
| TFA content | 13.5% |
| Water content | 3.1% |

The molar ratio of the starting material was determined using the following calculation:

$$\frac{\text{Teverelix content/molecular weight of teverelix}}{\text{TFA content/molecular weight of } TFA} \Rightarrow \frac{79.8/1459}{13.1/114} =$$

$$\frac{1}{2.16} = 1:2.16$$

The eight batches, one for each of the four molar ratios of 10 mg/ml, and one for each of the four molar ratios of 1 mg/ml, were prepared as follows.
Low Molar Ratio (1:1.7) at 10 mg/mL
1. 0.312 g of teverelix TFA (net weight teverelix) was reconstituted with water for injection, making the suspension up to 3.0 mL to form an 104 mg/mL homogenous milk suspension. Previous investigations demonstrate that at this concentration 96% of the teverelix will form solid teverelix, therefore approximately 300 mg of teverelix will be recovered as solid teverelix following centrifugation.
2. The preparation was immediately centrifuged for 10 minutes at 10,000 rpm (8,500 g) at 4° C.
3. The supernatant from the centrifuged material was discarded. Previous investigations have demonstrated that the solid teverelix has a molar ratio of approximately 1:1.7 teverelix to TFA.
4. The centrifugation pellet was resuspended with water for injection and made up to 30 mL to form a solution of approximately 10 mg/mL and a molar ratio of approximately 1:1.7.
Mid-Molar Range Ratio (1:2.16) at 10 mg/mL
1. 0.1 g of teverelix TFA (net weight teverelix) was reconstituted with water for injection in a 10 mL conical flask to make a solution of 10.0 mL volume to form a solution of teverelix at 10 mg/mL and a molar ratio of 1:2.16 teverelix to TFA.
High Molar Ratio (1:2.8) at 10 mg/mL
1. 0.1 g teverelix TFA (net weight teverelix) was reconstituted with 5 mL of 0.0097 M trifluoroacetic acid in water for injection in a 10 mL conical flask
2. The solution was made up to 10.0 mL with water for injection to form a solution of teverelix at 10 mg/mL and a molar ratio of 1:2.8 teverelix to TFA.
Extreme Molar Ratio (1:4.0) at 10 mg/mL
1. 0.1 g teverelix TFA (net weight teverelix) was reconstituted with 5 mL of 0.0252 M trifluoroacetic acid in water for injection in a 10 mL conical flask
2. The solution was made up to 10.0 mL with water for injection to form a solution of teverelix at 10 mg/mL and a molar ratio of 1:4.0 teverelix to TFA.
Low Molar Ratio (1:1.7) at 1 mg/mL
1. 0.312 g of teverelix TFA (net teverelix) was reconstituted with water for injection, making the suspension up to 3.0 mL to form an 104 mg/mL homogenous milk suspension.
2. The preparation was immediately centrifuged for 10 minutes at 10,000 rpm (8,500 g) at 4° C.
3. The supernatant from the centrifuged material was discarded
3. The centrifugation pellet was resuspended in water for injection (final volume 300 mL) to make up a solution of approximately 1 mg/mL and a molar ratio approximately 1:1.7 teverelix to TFA.
4. 10.0 mL was transferred to a 10 mL conical flask.
Mid-Molar Range Ratio (1:2.16) at 1 mg/mL
1. A 1 mg/mL solution of teverelix TFA in water for injection was prepared
High Molar Ratio (1:2.8) at 1 mg/mL
1. 0.010 g teverelix TFA (net weight teverelix) was reconstituted with 5 mL of a 0.001 M trifluoroacetic acid in water for injection in a 10 mL conical flask
2. The volume was completed to 10 mL with WFI
Extreme Molar Ratio (1:4.0) at 1 mg/mL
1. 0.010 g teverelix TFA (net weight teverelix) was reconstituted with 5 mL of a 0.0205 M trifluoroacetic acid in water for injection in a 10 mL conical flask
2. The volume was completed to 10 mL with WFI All of the solutions were kept at lab temperature (20° C.) before analyses for teverelix purity.

Samples was taken from each solution in duplicate and analysed for teverelix purity using a conventional RP-HPLC method. The chromatic conditions were as shown in table 10:

TABLE 10

| Column | Phenomenex Aqua C18 150 2.0 mm, 3 μm, 125Å, LCC-012 |
|---|---|
| Column temperature | 65° C. |
| Autosampler temperature | 4° C. |
| Flow rate | 0.3 ml/min |
| Injection volume | 3 μl |
| Run time | 60 minutes |
| Detection | UV detection, 226 nm |

The purity of teverelix in the solutions after preparation, i.e. at time zero, is shown in table 11:

TABLE 11

| Molar ratio | 10 mg/mL Time 0 | 1 mg/mL Time: 0 |
|---|---|---|
| 1:1.7 | 99.47% | 99.58% |
| 1:2.16 | 99.45% | 99.49% |
| 1:2.8 | 99.48% | 99.48% |
| 1:4.0 | 99.47% | 99.48% |

In order to evaluate the stability over time, the respective solutions were then stored in stoppered glass conical flasks in a chamber at +40° C. and a relative humidity of 75%.

After one month for the 10 mg/mL solutions, and two weeks for the 1 mg/mL solutions, teverelix purity analysis was repeated using the method already described. The purity of the solutions after the relevant period, is presented in table 12 below.

TABLE 12

| Molar ratio | 10 mg/mL Time: 1 month | 1 mg/mL Time: 15 days |
|---|---|---|
| 1:1.7 | 97.49% | 98.92% |
| 1:2.16 | 95.99% | 98.68% |

TABLE 12-continued

| Molar ratio | 10 mg/mL Time: 1 month | 1 mg/mL Time: 15 days |
|---|---|---|
| 1:2.8 | 93.49% | 98.37% |
| 1:4.0 | 86.16% | 97.97% |

Figure 6:
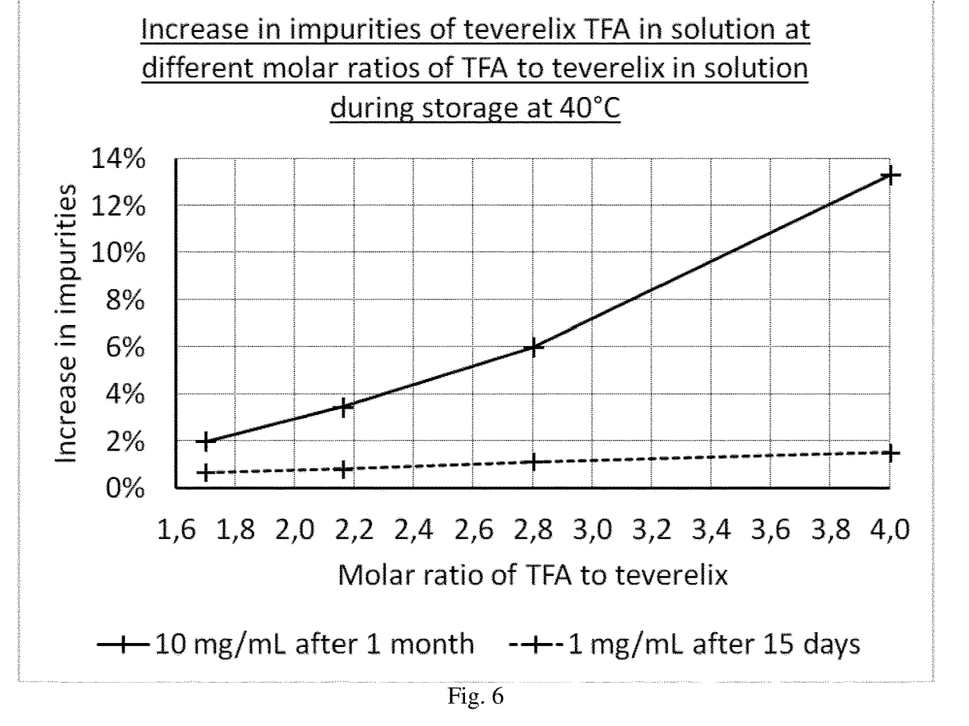
FIGS. 6 and 7 depict stability results in accordance with one or more embodiments of the present invention.
Figure 7:
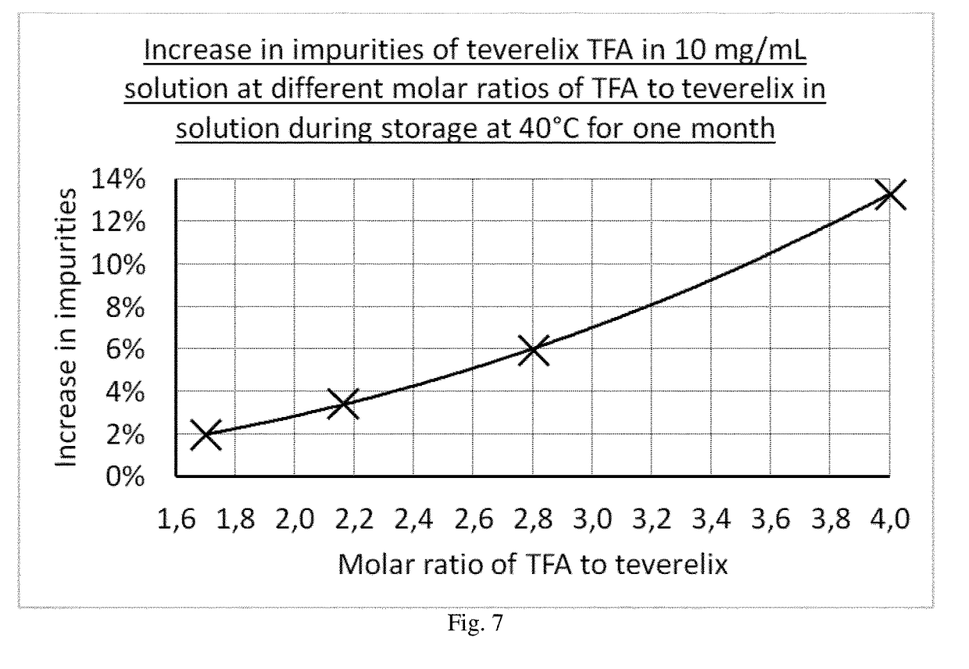

The stability results are shown in FIGS. 6 and 7, and depicts the increase in percentage of impurities during storage according to the molar ratio of the suspension. Note that the figures show the mol content of TFA per one mol teverelix.

From said figures it is clear that higher concentrations of trifluoroacetate in the solutions provides significantly higher concentrations of impurities, thus the results verify that when teverelix is placed in contact with increasing concentrations of acid (trifluoroacetate), undesirable degradation products (impurities) will appear in small amounts and may potentially influence quality, safety and efficacy of the formulation, thereby potentially causing serious health hazards. Thus, in order to obtain a stable teverelix-TFA lyophilisate, it is important to provide a composition with a low concentration/content of trifluoroacetate, i.e. for each mol of teverelix the molar content of trifluoroacetate should be kept as low as possible.

From FIGS. 6 and 7, it can be seen that when the molar ratio of teverelix to trifluoroacetate is below 1:2.8, (i.e. 1 mol teverelix to less than or equal to 2.8 mol TFA) in the suspension, the level of impurities, i.e. undesirable degradation products e.g. caused by deamidation are kept at an acceptable level.

It is also clear from said figures, that the concentration of teverelix is also relevant for the level of impurities. However, in order to reduce the injections volumes, it is relevant to have suspensions comprising concentrations of teverelix of at least 10 mg/ml preferably at least 30 mg/ml, thus it is not practically possible simply to reduce the concentration of teverelix in the final fluid, milky aqueous suspension. However, this factor makes the content of acid (trifluoroacetate) in the lyophilizate even more important during storage, as a low level of acid will provide a more stable product.

The compositions and formulations provided in the present invention is inexpensive to manufacture, and due to the ease of use they also provides a very simple dosage regime.

Modifications and combinations of the above principles and combinations are foreseen within the scope of the present invention.

The invention claimed is:

1. A lyophilization process for preparing a teverelix-TFA lyophilizate,
said process comprises the following steps:
a) providing a lyophilization suspension by mixing teverelix and trifluoroacetate at a molar ratio of teverelix to trifluoroacetate sufficient for providing a microcrystalline teverelix-TFA suspension without formation of a gel, and wherein the suspension comprises at least 2.1 mol trifluoroacetate per mol teverelix,
b) lyophilizating the lyophilization suspension from the step a) thereby providing a teverelix-TFA lyophilizate having a mol content of trifluoroacetate per mol teverelix which is lower than the mol content of trifluoroacetate per mol teverelix in the lyophilization suspension, wherein the step a) further comprises the following steps:

a') centrifuging or filtering the microcrystalline teverelix-TFA suspension thereby respectively providing a teverelix-TFA pellet or a teverelix-TFA filter cake with a a molar ratio of teverelix to TFA of 1:1.70 to 1:1.85, wherein the teverelix in the teverelix-TFA pellet or teverelix-TFA filter cake is microcrystalline, and
a") suspending said teverelix-TFA pellet or said teverelix-TFA filter cake in an aqueous suspension solution.

2. A lyophilization process according to claim 1, wherein the teverelix and trifluoroacetate in the step a) are mixed at a molar ratio of at least 1:2.2, such that for each mol teverelix in the composition the composition comprises at least 2.2 mol trifluoroacetate.

3. A lyophilization process according to claim 1, wherein the pellet after centrifuging or filter cake after filtering has a molar ratio of teverelix to trifluoroacetate which is lower than the molar ratio in the microcrystalline teverelix-TFA suspension.

4. A lyophilization process according to claim 1, wherein the aqueous suspension solution is water or a mannitol solution.

5. A lyophilization process according to claim 1, wherein the microcrystalline teverelix-TFA suspension is made in water if the molar ratio of teverelix to trifluoroacetate is at least 1:2.2, such that for each mol teverelix in the composition the composition comprises at least 2.2 mol trifluoroacetate.

6. A lyophilization process according to claim 1, wherein the microcrystalline teverelix-TFA suspension is made in a trifluroacetic acid solution if the molar ratio of teverelix to trifluoroacetate is below 1:2.2, such that for each mol teverelix in the composition the composition comprises below 2.2 mol trifluoroacetate.

7. A lyophilization process according to claim 1, wherein the teverelix-TFA lyophilizate from the step b) is sterilized by gamma-sterilisation.

8. A lyophilization process according to claim 1, wherein the concentration of teverelix-TFA in the microcrystalline teverelix-TFA suspension is at least 100 mg/ml.

9. A lyophilization process according to claim 1, wherein the resuspended pellet or resuspended filter cake is lyophilized or spray-dried to an extent such that the obtained teverelix-TFA lyophilizate comprises water in an amount between 0.3% and 5% by weight based on the total weight of the teverelix-TFA lyophilizate.

10. A lyophilization process according to claim 1, wherein the lyophilization is performed on a unit dosage of the teverelix-TFA lyophilizate and/or directly in the packaging for storage.

11. A method of reconstituting the teverelix-TFA lyophilizate obtained by claim 1, and wherein said method comprises adding an aqueous reconstitution solution to the teverelix-TFA lyophilizate and wherein said method further comprises adjusting the molar ratio by adding trifluoroacetate such that for each mol teverelix in the composition the composition comprises at least 2.1 mol trifluoroacetate.

12. A method according to claim 11, wherein the molar ratio of teverelix to trifluoroacetate is adjusted to at least 1:2.2, such that for each mol teverelix the composition comprises at least 2.2 mol trifluoroacetate.

13. A method according to claim 11, wherein the molar ratio of teverelix to trifluoroacetate is adjusted to be at or less than 1:2.8, such that for each mol teverelix the composition comprises at or less than 2.8 mol trifluoroacetate.

* * * * *